United States Patent
Orr et al.

(10) Patent No.: US 9,763,601 B2
(45) Date of Patent: Sep. 19, 2017

(54) DETERMINING COMPONENTS OF TOTAL CARBON DIOXIDE EXCRETED BY A SUBJECT

(75) Inventors: Joseph Allen Orr, Park City, UT (US); Lara Brewer, Bountiful, UT (US)

(73) Assignee: Koninklijke Philips N.V., Eindhoven (NL)

( * ) Notice: Subject to any disclaimer, the term of this patent is extended or adjusted under 35 U.S.C. 154(b) by 799 days.

(21) Appl. No.: 13/636,526

(22) PCT Filed: Mar. 17, 2011

(86) PCT No.: PCT/IB2011/051123
§ 371 (c)(1),
(2), (4) Date: Sep. 21, 2012

(87) PCT Pub. No.: WO2011/121473
PCT Pub. Date: Oct. 6, 2011

(65) Prior Publication Data
US 2013/0013281 A1   Jan. 10, 2013

Related U.S. Application Data

(60) Provisional application No. 61/319,446, filed on Mar. 31, 2010.

(51) Int. Cl.
*A61B 5/083* (2006.01)
*A61M 16/00* (2006.01)
*A61B 5/00* (2006.01)

(52) U.S. Cl.
CPC .......... *A61B 5/0836* (2013.01); *A61B 5/412* (2013.01); *A61M 16/0003* (2014.02)

(58) Field of Classification Search
CPC .................................................. A61B 5/0836
See application file for complete search history.

(56) References Cited

U.S. PATENT DOCUMENTS 6,402,697 B1 * 6/2002 Calkins ............... A61B 5/0836
                                                            600/529
6,540,689 B1  4/2003 Orr et al.
(Continued)

FOREIGN PATENT DOCUMENTS

JP    2009207874 A    9/2009
WO    0042908 A1      7/2000
(Continued)

OTHER PUBLICATIONS

Chonan et al. "Rate of Elimination of Excess CO2 in Humans." Respiration Physiology, vol. 73, No. 3, Sep. 1988, pp. 379-394.*
Andreassen et al. "Mathematical models of oxygen and carbon dioxide storage and transport: interstitial fluid and tissue stores and whole-body transport." Crit Rev Biomed Eng. 2005;33(3):265-98.*
(Continued)

*Primary Examiner* — Meredith Weare

(57) ABSTRACT

Values of components of total carbon dioxide excreted by a subject can be provided. One or more signals may be received conveying information related to a rate of total carbon dioxide excreted by the subject. Based at least in part on the received one or more signals, a first capnometric component and/or a second capnometric component may be determined. The first capnometric component may indicate a rate of metabolic carbon dioxide production. The second capnometric component may indicate a rate of carbon dioxide transfer to or from body compartments of the subject that store carbon dioxide. The first capnometric component and/or the second capnometric component may be presented to a user.

13 Claims, 3 Drawing Sheets

(56) References Cited

U.S. PATENT DOCUMENTS

| | | | |
|---|---|---|---|
| 6,955,651 B2* | 10/2005 | Kuck et al. | 600/532 |
| 7,074,196 B2* | 7/2006 | Kuck et al. | 600/532 |
| 7,699,788 B2* | 4/2010 | Kuck et al. | 600/532 |
| 8,398,559 B2* | 3/2013 | Kuck et al. | 600/532 |
| 2002/0183643 A1* | 12/2002 | Kuck et al. | 600/532 |
| 2004/0199083 A1* | 10/2004 | Mault | A61B 5/0833 600/532 |
| 2005/0124907 A1* | 6/2005 | Kuck et al. | 600/532 |
| 2005/0177055 A1* | 8/2005 | Kuck et al. | 600/532 |
| 2006/0253038 A1* | 11/2006 | Kuck et al. | 600/484 |
| 2008/0194980 A1* | 8/2008 | Gisolf | A61B 5/029 600/526 |
| 2010/0179392 A1* | 7/2010 | Chang | A61B 5/0205 600/301 |
| 2013/0013281 A1 | 1/2013 | Orr et al. | |
| 2013/0267863 A1* | 10/2013 | Orr | 600/532 |

FOREIGN PATENT DOCUMENTS

| | | |
|---|---|---|
| WO | 0108554 A1 | 2/2001 |
| WO | 2006049485 A1 | 5/2006 |

OTHER PUBLICATIONS

Rees et al. "Using physiological models and decision theory for selecting appropriate ventilator settings." J Clin Monit Comput. Dec. 2006;20(6):421-9. Epub Sep. 15, 2006.*

"Finite State Machine." The American Heritage Science Dictionary. 2002.*

Chonan, T. et al "Rate of Elimination of Excess CO2 in Humans" Respiration Physiology, vol. 73, No. 3, Sep. 1988, pp. 379-394.

Chiari, Lorenzo et al "A Comprehensive Simulator of the Human Respiratory System: Validation with Experimental and Simulated Data", Annals of Biomedical Engineering, vol. 25, No. 6, Dec. 1997, pp. 985-999.

Ursino, Mauro et al "An Integrated Model of the Human Ventilatory Control System: The Response to Hypercapnia", Clinical Physiology, vol. 21, No. 4, 2001, pp. 447-464.

Farhi, Leon E. et al "Dynamics of Changes in Carbon Dioxide Stores", Anesthesiology, vol. 21, No. 6, Nov.-Dec. 1960, pp. 604-614.

Farhi, L.E. et al., "Dynamics of Changes in Carbon Dioxide Stores", Anesthesiology, vol. 21, No. 6, 1960, pp. 604-614.

Chonan, T., et al., "Rate of elimination of excess CO2 in Humans", Respitory Physiology, vol. 73, No. 3, 1988.

* cited by examiner

DETERMINING COMPONENTS OF TOTAL CARBON DIOXIDE EXCRETED BY A SUBJECT

BACKGROUND OF THE INVENTION

1. Field of the Invention

The invention relates to providing values of components of total carbon dioxide excreted by a subject.

2. Description of the Related Art

Carbon dioxide ($CO_2$) excretion monitoring is done, for example, to assess the adequacy of mechanical ventilation and the rate of metabolism in critical care subjects. Carbon dioxide excretion measurements are generally made by integrating respiratory flow and carbon dioxide signals over time. Carbon dioxide is a natural by-product of metabolism and is excreted with every breath. The human body stores a large amount of carbon dioxide in tissues as dissolved gas, bound to bicarbonate, and/or in other forms. As such, a measured carbon dioxide excretion rate reflects the sum of the metabolically produced carbon dioxide and the rate of carbon dioxide transfer to or from the carbon dioxide stores in the body. Carbon dioxide excretion is often expressed as the volume of excreted carbon dioxide per minute, and may be represented as $V_{CO_2}$. Typically, a human excretes approximately 200 mL of carbon dioxide per minute.

The rate of metabolic carbon dioxide production is proportional to whole-body metabolic activity. If the exact substrate utilization is known, respiratory quotient (RQ) can be estimated and energy expenditure can be calculated directly from the metabolic carbon dioxide production rate. Metabolic carbon dioxide production increases with increasing caloric expenditure caused by accelerated physical activity, increased respiratory effort, sepsis, malignant hyperthermia etc. Metabolic carbon dioxide production decreases in response to a decrease in metabolic activity caused by a decrease in subject work or organ failure.

Transfer of carbon dioxide to, or from, the tissue stores follows a change in effective ventilation. An increase in ventilation causes an increase in carbon dioxide excretion. In this situation, carbon dioxide excretion represents the sum of carbon dioxide released from the stores plus metabolically produced carbon dioxide. A decrease in effective ventilation causes a fall in rate of carbon dioxide excretion. When the body is unable to excrete all of the metabolically produced carbon dioxide, the measured carbon dioxide excretion is the metabolically produced carbon dioxide less the amount is transferred to the stores. The rate at which carbon dioxide is added to, or released from, the stores indicates the rate of change in the partial pressure of arterial carbon dioxide ($PaCO_2$). The transfer of carbon dioxide to and from the stores following changes in ventilation or metabolic rate continues for an extended period depending on subject size, cardiac output etc.

When a subject is over-ventilated, measured carbon dioxide excretion is in excess of metabolic carbon dioxide production and carbon dioxide is being "blown off," or removed, from the carbon dioxide stored in the tissues, which leads to a reduction in arterial carbon dioxide. When a subject is under-ventilated, carbon dioxide excretion is inadequate to clear all of the metabolically created carbon dioxide, so carbon dioxide accumulates in the tissues, causing arterial carbon dioxide to rise.

When ventilation and metabolic rate have been stable for a long time (1-2 hours depending on the subject and conditions) then the measured carbon dioxide excretion is approximately equal to the rate of metabolically produced carbon dioxide. By definition, this is the period of steady state when carbon dioxide is not being transferred to or from the tissue stores and therefore the measured carbon dioxide excretion solely reflects the carbon dioxide from metabolism. In many critical care situations, however, ventilation is unstable such that the measured carbon dioxide excretion is the sum of metabolically produced carbon dioxide and transfers to or from carbon dioxide stores.

The utility of measured carbon dioxide excretion as a clinically monitored parameter is limited because the measured rate of carbon dioxide excretion is the sum of metabolic carbon dioxide production and transfer of carbon dioxide to or from tissue stores. In the presently available volumetric capnometry products, there is no way in a clinical setting to separate the rate of metabolic carbon dioxide production from the rate of carbon dioxide transfer to and from the tissue carbon dioxide stores.

SUMMARY OF THE INVENTION

One aspect of the invention relates to a method for providing values of components of total carbon dioxide excreted by a subject. The method may include receiving one or more signals conveying information related to a rate of total carbon dioxide excreted by the subject. The method may also include determining, based at least in part on the received one or more signals, a first capnometric component indicating a rate of metabolic carbon dioxide production. The method may further include determining, based at least in part on the received one or more signals, a second capnometric component indicating a rate of carbon dioxide transfer to or from body compartments of the subject that store carbon dioxide. In addition, the method may include presenting one or more of the first capnometric component or the second capnometric component to a user.

Another aspect of the invention relates to a system for providing values of components of total carbon dioxide excreted by a subject. The system may include one or more processors configured to execute computer program modules. The computer program modules may include a data acquisition module, a component determination module, and/or a capnometry display module. The data acquisition module may be configured to receive one or more signals conveying information related to a rate of total carbon dioxide excreted by the subject. The component determination module may be configured to determine, based at least in part on the received one or more signals, a first capnometric component indicating a rate of metabolic carbon dioxide production and/or a second capnometric component indicating a rate of carbon dioxide transfer to or from body compartments of the subject that store carbon dioxide. The capnometry display module may be configured to provide, for presentation to a user, one or more of the first capnometric component or the second capnometric component.

Yet another aspect of the invention relates to a system for providing values of components of total carbon dioxide excreted by a subject. The system may include data acquisition means for receiving one or more signals conveying information related to a rate of total carbon dioxide excreted by the subject. The system may also include component determination means for determining, based at least in part on the received one or more signals, a first capnometric component indicating a rate of metabolic carbon dioxide production and/or a second capnometric component indicating a rate of carbon dioxide transfer to or from body compartments of the subject that store carbon dioxide. The system may further include display means for presenting one or more of the first capnometric component or the second capnometric component to a user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
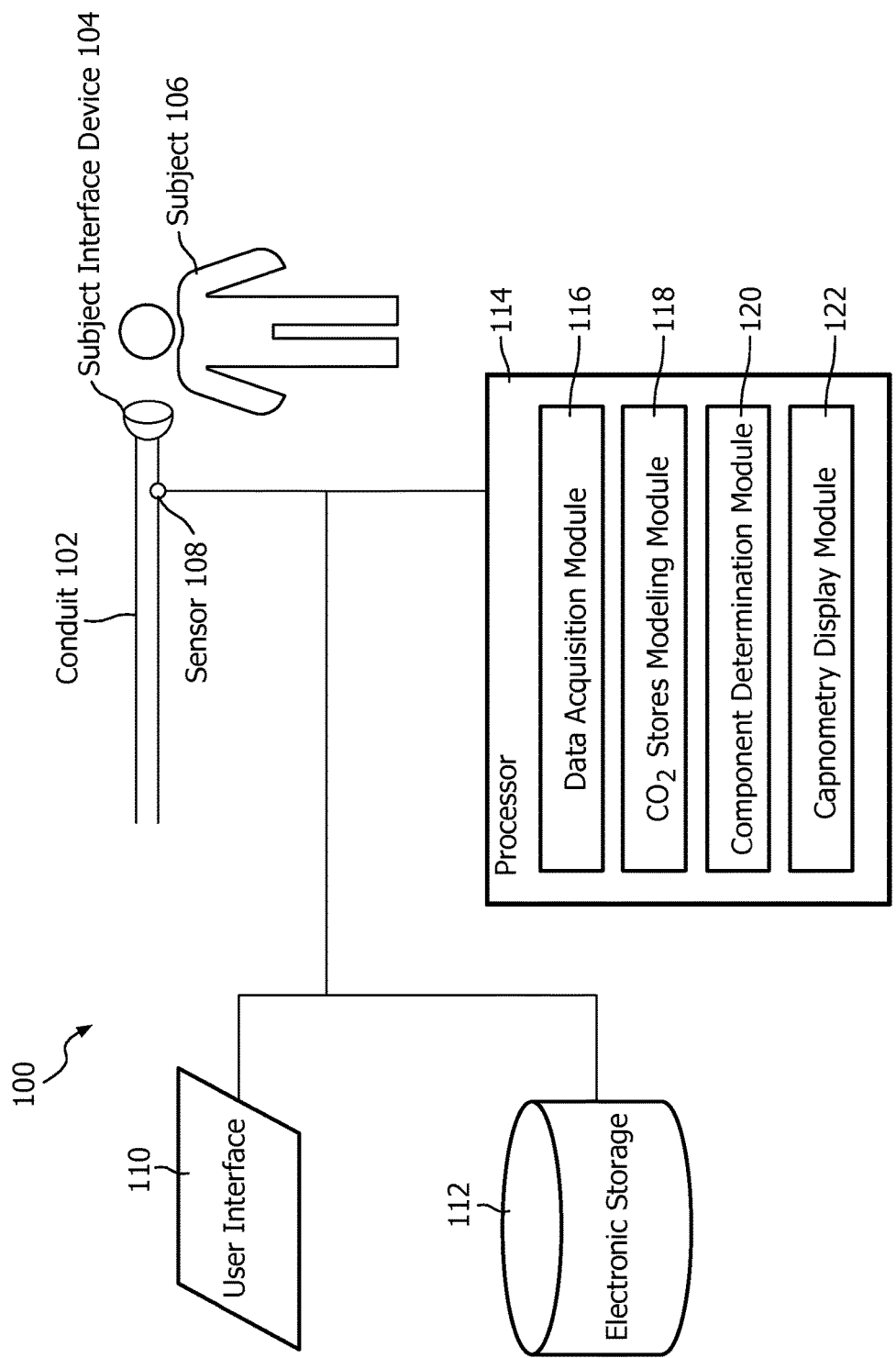
FIG. 1 illustrates an exemplary system for providing values of components of total carbon dioxide excreted by a subject.

FIG. 1 illustrates an exemplary system 100 for providing values of components of total carbon dioxide excreted by a subject. According to embodiments of the invention, the system 100 uses a model of carbon dioxide production, distribution, and/or excretion in a subject's body to separate the rate of metabolically produced carbon dioxide from the rate of carbon dioxide transferred to and from the body tissue stores. The rate of metabolically produced carbon dioxide and/or the rate of carbon dioxide transferred to and from the body tissue stores may be determined in real-time or near real-time. Separating the rate of carbon dioxide excretion into these two component rates makes the rate of carbon dioxide excretion a more understandable and useful parameter. For example, separating measured carbon dioxide excretion rate into its component parts before display on a monitor screen makes this parameter more useful for treating critical care subjects that are being mechanically ventilated either invasively or non-invasively. As depicted in FIG. 1, the system 100 includes a conduit 102 coupled with a subject interface device 104 for delivering respiratory gases to a subject 106. A sensor 108 is coupled with the conduit 102 and/or the subject interface device 104 to detect one or more characteristics of gas contained therein. The system 100 further includes a user interface 110, electronic storage 112, and a processor 114.

The conduit 102 is configured to place the subject interface device 104 in fluid communication with a source of a respiratory gas or other breathable substance. For example, a flow of breathable gas may be delivered to the subject 106 through the conduit 102 having one or more parameters that are controlled in accordance with a therapy regime. The one or more parameters of the flow of breathable gas that are controlled may include one or more of pressure, flow rate, composition, humidity, temperature, and/or other parameters.

The subject interface device 104 may engage one or more orifices of the airway of the subject 106 in a sealed or unsealed manner. Some examples of the subject interface device 104 may include, for example, an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present invention is not limited to these examples, and contemplates implementation of any subject interface.

The sensor 108 is configured to generate output signals conveying information related to one or more parameters of the gas within the conduit 102 and/or the subject interface device 104. By way of non-limiting example, the one or more parameters of the gas may include composition, pressure, flow rate, and/or other parameters. The sensor 108 may be configured to determine various parameters relating to the subject such as, for example, breath rate, breath volume, dead space measures, cardiac output, and/or other parameters relating to the subject. In some embodiments, the sensor 108 includes a capnometer for determining concentration or partial pressure of carbon dioxide in respiratory gases. Generally speaking, capnometers operate on the principle that carbon dioxide absorbs infrared radiation. A beam of infrared light may be passed across a gas sample to fall on to an infrared sensor. The presence of carbon dioxide in the gas leads to a reduction in the amount of light falling on the infrared sensor, which changes the voltage in a circuit. The present invention is not limited to these examples, and contemplates implementation of any carbon dioxide sensor.

It will be appreciated that the illustration of the sensor 108 in FIG. 1 as a single component is not intended to be limiting. In one embodiment, the sensor 108 includes a plurality of sensors. Further, the location of the sensor 108 relative to the conduit 102 and/or the subject interface device 104 is not intended to be limiting. The sensor 108 may include one or more sensing units disposed in the conduit 102, the subject interface device 104, at the source of the breathable substance, and/or disposed at other locations in the system 100.

The user interface 110 is configured to provide an interface between the system 100 and a user (e.g., the user, a caregiver, a therapy decision-maker, etc.) through which the user may provide information to and receive information from the system 100. This enables data, results, and/or instructions and any other communicable items, collectively referred to as "information," to be communicated between the user and the system 100. Examples of interface devices suitable for inclusion in the user interface 110 include a keypad, buttons, switches, a keyboard, knobs, levers, a display screen, a touch screen, speakers, a microphone, an indicator light, an audible alarm, and a printer.

It is to be understood that other communication techniques, either hard-wired or wireless, are also contemplated by the present invention as the user interface 110. For example, the present invention contemplates that the user interface 110 may be integrated with a removable storage interface provided by the electronic storage 112. In this example, information may be loaded into the user interface 110 from removable storage (e.g., a smart card, a flash drive, a removable disk, etc.) that enables the user(s) to customize the implementation of the user interface 110. Other exemplary input devices and techniques adapted for use with the system 100 as the user interface 110 include, but are not limited to, an RS-232 port, RF link, an IR link, modem (telephone, cable or other). In short, any technique for communicating information with the system 100 is contemplated by the present invention as the user interface 110.

According to exemplary embodiments, the electronic storage 112 includes electronic storage media that electronically stores information. The electronic storage media of the electronic storage 112 may include one or both of system storage that is provided integrally (i.e., substantially non-removable) with the system 100 and/or removable storage that is removably connectable to the system 100 via, for example, a port (e.g., a USB port, a firewire port, etc.) or a drive (e.g., a disk drive, etc.). the electronic storage 112 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storage 112 may store software algorithms, information determined by the processor 114, information received via the user interface 110, and/or other information that enables the system 100 to function properly. The electronic storage 112 may be a separate component within the system 100, or the electronic storage 112 may be provided integrally with one or more other components of the system 100 (e.g., the processor 114).

The processor 114 is configured to provide information processing capabilities in the system 100. As such, the processor 114 may include one or more of a digital processor, an analog processor, a digital circuit designed to process information, an analog circuit designed to process information, a state machine, and/or other mechanisms for electronically processing information. Although the processor 114 is shown in FIG. 1 as a single entity, this is for illustrative purposes only. In some implementations, the processor 114 may include a plurality of processing units. These processing units may be physically located within the same device, or the processor 114 may represent processing functionality of a plurality of devices operating in coordination.

As is shown in FIG. 1, the processor 114 is configured to execute one or more computer program modules. The one or more computer program modules may include one or more of a data acquisition module 116, a carbon dioxide stores modeling module 118, a component determination module 120, a capnometry display module 122, and/or other modules. The processor 114 may be configured to execute modules 116, 118, 120, and/or 122 by software; hardware; firmware; some combination of software, hardware, and/or firmware; and/or other mechanisms for configuring processing capabilities on the processor 114.

It should be appreciated that although modules 116, 118, 120, and 122 are illustrated in FIG. 1 as being co-located within a single processing unit, in implementations in which the processor 114 includes multiple processing units, one or more of the modules 116, 118, 120, and/or 122 may be located remotely from the other modules. The description of the functionality provided by the different modules 116, 118, 120, and/or 122 described below is for illustrative purposes, and is not intended to be limiting, as any of modules 116, 118, 120, and/or 122 may provide more or less functionality than is described. For example, one or more of the modules 116, 118, 120, and/or 122 may be eliminated, and some or all of its functionality may be provided by other ones of the modules 116, 118, 120, and/or 122. As another example, the processor 114 may be configured to execute one or more additional modules that may perform some or all of the functionality attributed below to one of the modules 116, 118, 120, and/or 122.

The data acquisition module 116 may be configured to receive one or more signals conveying information related to a rate of total carbon dioxide excreted by the subject. These received one or more signals may convey information related to the rate of total carbon dioxide excreted by the subject in real time or near real time. Information contained in the one or more received signals may be stored by the electronic storage 112, and may be subsequently recalled by the processor 114 (or modules thereof) for carrying out various operations described herein.

The carbon dioxide stores modeling module 118 may be configured to model one or more body compartments of the subject. More specifically, a model of carbon dioxide production, distribution, and/or excretion in one or more body compartments is implemented to identify the rate of metabolic carbon dioxide production. An example of such a model is described in "Dynamics of Changes in CO2 Stores" by L. E. Farhi and H. Rahn (Anesthesiology, 21:6, November-December 1960, pp. 604-614), which is incorporated by reference into this disclosure. The modeled one or more body compartments may include one or more of the heart, the lungs, the brain, the blood, the muscle, the fat, the kidneys, and/or other body compartments. The volume of each of these body compartments can be selected based on manually entered body weight and published anatomic norms. For example, body weight, height, and/or other physical parameters of subject 106 may be input to system 100 through user interface 110. The proportion with which each body compartment produces and stores carbon dioxide is published in various physiologic studies. According to some embodiments, the carbon dioxide stores modeling module 118 may be further configured to utilize previously received information related to the rate of total carbon dioxide excreted by the subject to tune one or more model parameters relating to the modeled one or more body compartments, as described further herein.

The model implemented by the carbon dioxide stores modeling module 118 may assume that whole-body metabolic carbon dioxide production and cardiac output is fixed for a certain period (e.g., 15-60 minutes) depending on model settings. During this period in which respiration data has been stored such as by the electronic storage 112, the model may process breath-by-breath alveolar minute ventilation data, which may be provided by the sensor 108, sequentially to predict the excreted carbon dioxide for each breath. For one or more parameters of the model, multiple values may be used for a plurality of predictions for carbon dioxide excretion for each breath in order to tune the parameters of the model for subject 106. For example, multiple values of metabolic carbon dioxide production may be tested by the model to find one value that causes the model to best match the observed data during the test period. Although a less computationally demanding search algorithm may be employed without departing from the scope of this disclosure, exemplary embodiments of the present invention use a global search of all possible values within a range to find the value of metabolic carbon dioxide production that best explains the observed carbon dioxide excretion measurements. The model implemented by the carbon dioxide stores modeling module 118 may invoke algorithms relating to one or more of gradient descent, Newton's method, $R_{prop}$, and/or other algorithms, in accordance with some embodiments.

In some embodiments, the model implemented by the carbon dioxide stores modeling module 118 may be quite sensitive to selection of a precise value of metabolic carbon dioxide production. As such, even a small difference between the selected and actual metabolic carbon dioxide production rate may cause the model to accumulate, or deplete, carbon dioxide in the modeled stores. Because these errors are cumulative, even small errors lead to large differences in modeled and actual metabolic carbon dioxide production when analyzed over the course of the analyzed epoch which corresponds to hundreds of analyzed breaths.

In typical operation, a user of the system 100 may connect subject interface device 104 to the subject, thereby placing the sensor 108 in communication with respiratory gases inhaled and exhaled by the subject. The subject's weight and estimated cardiac output may also be inputted by the user, such as via the user interface 110. The sensor 108 then collects breath-by-breath minute ventilation, dead space ventilation, and carbon dioxide excretion data until enough data needed for processing in the model has been collected and stored by the electronic storage 112. According to some embodiments, after sufficient data has been collected, the model is used to analyze the data from the past 15-60 minutes to select the value of metabolic carbon dioxide production and/or other parameters that, when used as input to the model, minimizes the difference between the modeled and actual carbon dioxide excretion over the period of analysis. As new data is gathered by the sensor 108, this process is repeated and the value of metabolic carbon dioxide production and/or other parameters of the model are obtained in an ongoing manner.

According to exemplary embodiments, the model implemented by the carbon dioxide stores modeling module 118 is tuned to match the measured carbon dioxide excretion, rather than the end-tidal carbon dioxide. End-tidal carbon dioxide is the maximum concentration of carbon dioxide that is observed during the expiratory phase of the breath. When tidal volume is adequate to completely clear the anatomic and apparatus dead space, and when there are no regions of the lung that are inadequately perfused, end-tidal carbon dioxide is a measure of alveolar, or end-capillary, carbon dioxide. In addition of inadequate breath size and alveolar dead space, intrapulmonary shunts can further distort the relationship between arterial and end tidal carbon dioxide partial pressure.

Carbon dioxide excretion measured at or near the mouth by the sensor 108 corresponds to the full of amount of carbon dioxide that leaves the body for every breath. The presence of ventilation/perfusion mismatch or inadequate breath size may not impact the accuracy of the carbon dioxide excretion measurement. As such, tuning the model implemented by the carbon dioxide stores modeling module 118 to model measurements of carbon dioxide excretion may be more reliable than tuning the model to end-tidal carbon dioxide measurements, even in the presence of lung pathologies.

The component determination module 120 may be configured to determine various components of the total carbon dioxide excreted by the subject. Such a determination may be based at least in part on the one or more signals received by the data acquisition module 116. Determinations made by the component determination module 120 may be performed in real-time or near real-time. In exemplary embodiments, the component determination module 120 may be further configured to utilize the modeled one or more body compartments for determining one or more of the first capnometric component or the second capnometric component. As discussed above, one example of a component determined by the component determination module 120 may include a first capnometric component indicating a rate of metabolic carbon dioxide production. Another example of a component determined by the component determination module 120 may include a second capnometric component indicating a rate of carbon dioxide transfer to or from body compartments of the subject that store carbon dioxide. Based on the model implemented by the carbon dioxide stores modeling module 118, a simple calculation may be utilized to determine the first component and/or the second component, since the rate of the total amount of carbon dioxide excreted by a subject is equal to the summation of the rate of metabolic carbon dioxide production and the rate of carbon dioxide transfer to or from body compartments of the subject that store carbon dioxide.

The capnometry display module 122 may be configured to provide, for presentation to a user, the first capnometric component, the second capnometric component, values derived from or related to the first capnometric component and/or the second capnometric component, and/or other information associated with carbon dioxide excretion. Such information may be presented via the user interface 110 or other mechanism for conveying information to the user. In exemplary embodiments, the excreted carbon dioxide parameter is displayed as two separate components. The first is the metabolic carbon dioxide production, which may be used as an indicator of global energy expenditure and metabolic activity. The next displayed component is the rate of carbon dioxide transfer to, or from, the stores. A positive flow of carbon dioxide to the stores is indicative of rising arterial carbon dioxide and possible under-ventilation. Conversely, a negative carbon dioxide transfer rate is indicative of falling arterial carbon dioxide and possible over-ventilation. The sum of the metabolic carbon dioxide production and the carbon dioxide accumulation (or depletion) in the body stores, which is equal to the measured carbon dioxide excretion, may also be displayed. Information associated with carbon dioxide excretion may be presented to a user in various way such as, for example, as a graph plotted against time, a graph plotted against expired volume, numerically, and/or via any other data representation schemes.

The metabolic carbon dioxide production may be a fairly stable value that does not respond to rapid changes in respiratory rate or tidal volume. The carbon dioxide stores transfer rate responds rapidly and transiently to ventilation changes. For example, an increase in alveolar minute ventilation may cause an immediate increase in carbon dioxide stores transfer that would slowly decrease over the subsequent minutes or hours, while the metabolic carbon dioxide production would remain unchanged in response to the same ventilation change. The magnitude and duration of the carbon dioxide stores transfer component, when shown on trend plot, is indicative of the magnitude of the change in arterial carbon dioxide caused by the ventilation change. It is noteworthy that arterial carbon dioxide is stable when the carbon dioxide stores transfer parameter is at or near zero. A value of carbon dioxide stores transfer that is at or near zero indicates that arterial carbon dioxide is unchanging.

Figure 2:
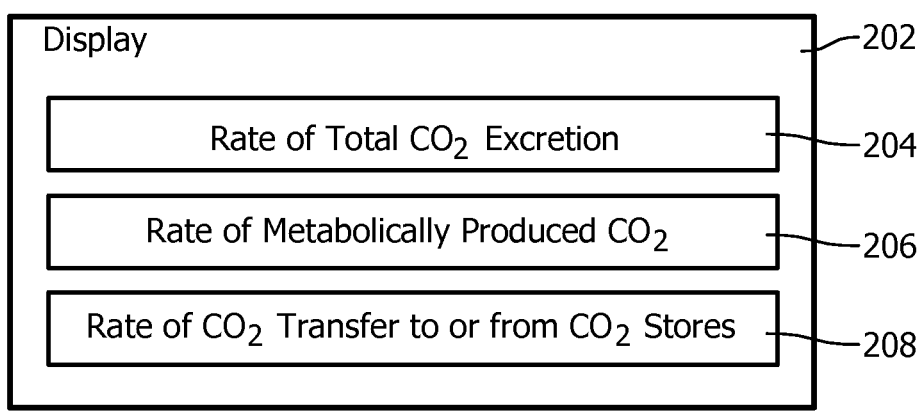
FIG. 2 illustrates an exemplary display for conveying, among other information, values of components of total carbon dioxide excreted by a subject.

FIG. 2 illustrates a display 202 for conveying, among other information, values of components of total carbon dioxide excreted by the subject 106, in accordance with exemplary embodiments. As depicted, the display 202 shows a rate of total carbon dioxide excretion 204, a rate of metabolically produced carbon dioxide 206, and a rate of carbon dioxide transfer to or from carbon dioxide stores 208. Information presented by the display 202 may be in a variety of forms such as graphical, numerical, or other forms of data representation.

Figure 3:
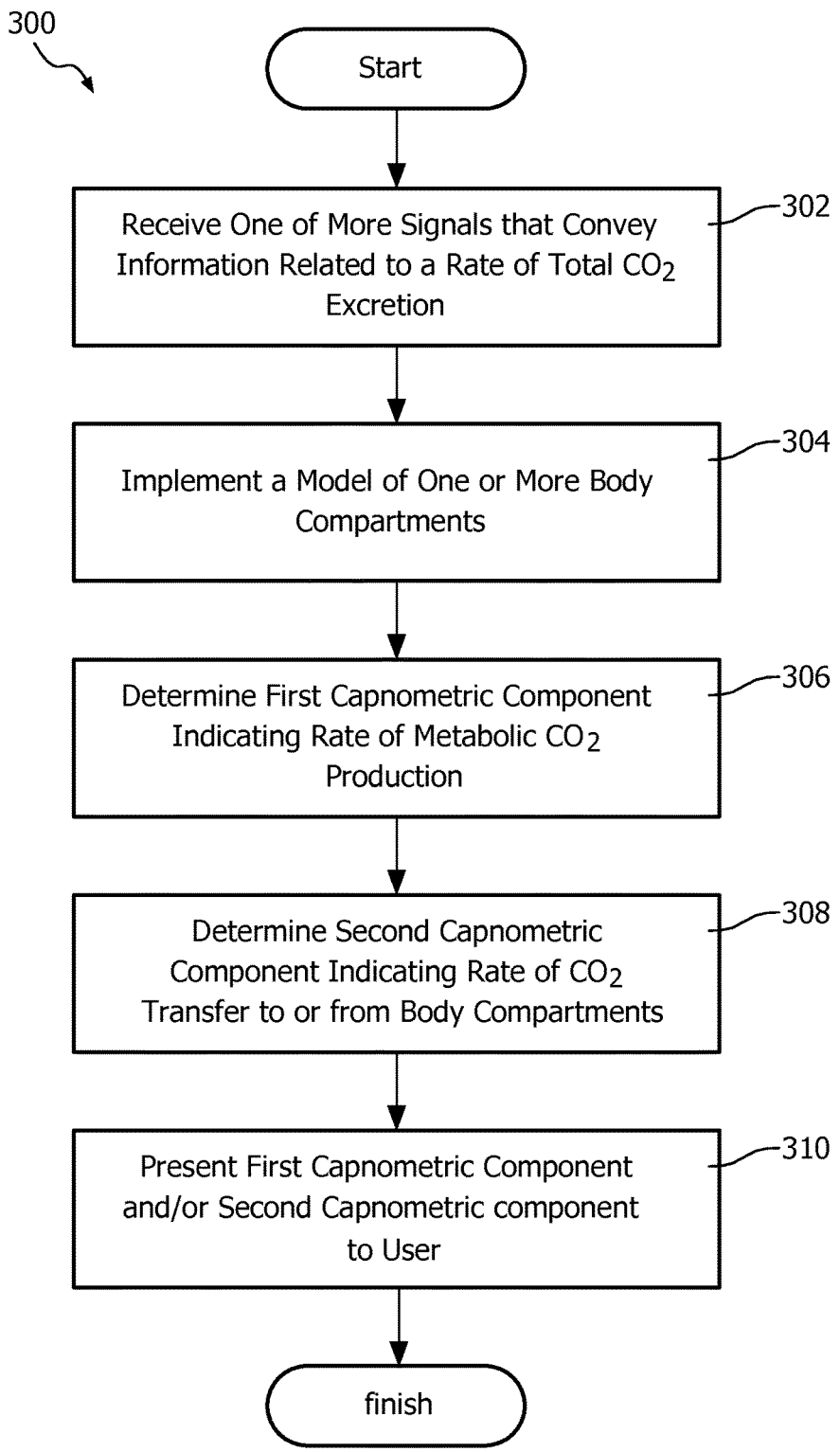
FIG. 3 is a flow chart illustrating an exemplary method for providing values of components of total carbon dioxide excreted by a subject.

FIG. 3 is a flow chart illustrating an exemplary method 300 for providing values of components of total carbon dioxide excreted by a subject. The operations of the method 300 presented below are intended to be illustrative. In some implementations, the method 300 may be accomplished with one or more additional operations not described, and/or without one or more of the operations discussed. Additionally, the order in which the operations of the method 300 are illustrated in FIG. 3 and described below is not intended to be limiting.

In some implementations, the method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of the method 300 in response to instructions stored electronically on an electronic storage medium. The one or more processing devices may include one or more devices configured through hardware, firmware, and/or software to be specifically designed for execution of one or more of the operations of the method 300.

At an operation 302, one or more signals are received that convey information related to a rate of total carbon dioxide excreted by a subject (e.g., the subject 106). According to some embodiments, the received one or more signals may convey information related to the rate of total carbon dioxide excreted by the subject in real time or near real time. The one or more signal may be received from the sensor 108 by the data acquisition module 116.

At an operation 304, a model is implemented of one or more body compartments of the subject. The model may determine one or more of carbon dioxide production, carbon dioxide distribution, or carbon dioxide excretion of one or more body compartments of the subject. The modeled one or more body compartments may include one or more of the heart, the lungs, the brain, the blood, the muscle, the fat, the kidneys, and/or other compartments. The various ones of the one or more modeled body compartments may be modeled individually or in combination with other compartments. In exemplary embodiments, the model may utilize previously received information related to the rate of total carbon dioxide excreted by the subject to tune one or more model parameters relating to the modeled one or more body compartments. The operation 304 may be performed by the carbon dioxide stores modeling module 118, according to some embodiments.

At an operation 306, first capnometric component indicating a rate of metabolic carbon dioxide production is determined. The determination of operation 306 may be based at least in part on the one or more signals received at operation 302. The determination of operation 306 may be based at least in part on the model implemented at operation 304. The first capnometric component may be determined in real-time or near real-time. In exemplary embodiments, the component determination module 120 may be executed to perform operation 306.

At an operation 308, a second capnometric component indicating a rate of carbon dioxide transfer to or from body compartments of the subject that store carbon dioxide is determined. The determination of operation 308 may be based at least in part on the one or more signals received at operation 302. The determination of operation 308 may be based at least in part on the model implemented at operation 304. The second capnometric component may be determined in real-time or near real-time. Operation 308 may be performed through execution of the component determination module 120, according to some embodiments.

At an operation 310, the first capnometric component (determined at operation 306) and/or the second capnometric component (determined at operation 308) are presented to a user. In accordance with exemplary embodiments, the capnometry display module 122 may be executed to perform operation 310.

Embodiments of the present invention may be implemented for a variety of applications such as, by way of non-limiting example, in non-invasive positive pressure ventilation (NPPV) and/or in determining ventilator settings. Carbon dioxide monitoring during non-invasive positive pressure ventilation presents a challenge for multiple reasons. First, it may be difficult to acquire an accurate measurement of end-tidal carbon dioxide because gas flow from the ventilator during expiration dilutes the alveolar gas sample. Furthermore, even when a pure alveolar (end-tidal) gas sample is analyzed, the relationship between observed expired carbon dioxide and actual arterial carbon dioxide may be questionable when ventilation perfusion mismatches are present or suspected. If an accurate rate of carbon dioxide excretion measurement is possible, then monitoring of the transfer of carbon dioxide to and from the tissue stores can be used to directly assess the rate at which the non-invasive positive pressure ventilation is reducing arterial carbon dioxide, or if the non-invasive positive pressure ventilation is failing to remove stored carbon dioxide and arterial carbon dioxide is rising. So long as all of the excreted carbon dioxide is measured by the sensor 108, then the direction and rate of arterial carbon dioxide changes can be non-invasively monitored continuously without the need for arterial blood gas analysis.

As mentioned above, another application of embodiments of the present invention includes determining ventilator settings. This may be performed by calculating the metabolically produced carbon dioxide as an input to various equations needed to select the respiratory rate in mechanically ventilated subjects. Such calculations may enhance the care of subjects that are on ventilation protocols in which smaller tidal volumes are indicated. The respiratory rate recommended by the system may therefore be the rate required to achieve adequate alveolar minute ventilation in the face of ventilation-perfusion inequality that is tied to a desired arterial carbon dioxide. The calculations take into account the amount of carbon dioxide that a subject creates (metabolic carbon dioxide production) and the amount of carbon dioxide that is excreted with each breath in order to calculate the necessary respiratory rate that is needed to achieve any desired arterial carbon dioxide partial pressure. The inputs to such a calculation (e.g., tidal volume, airway dead volume, VD/VT ratio, and/or metabolically produced carbon dioxide) may also be available as monitored parameters using the sensor 108.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method for providing values of components of total carbon dioxide excreted by a subject with a system comprising a carbon dioxide sensor, one or more hardware processors configured by machine readable instructions, and a display, the method comprising:
    receiving, with the one or more hardware processors from the carbon dioxide sensor, one or more signals conveying information related to a rate of total carbon dioxide excreted by the subject to determine a measured carbon dioxide excretion that corresponds to a full amount of carbon dioxide that leaves the subject for every breath, the measured carbon dioxide being a sum of metabolic carbon dioxide production and carbon dioxide released from tissue stores of the subject,
    determining, with the one or more hardware processors, based at least in part on (i) the received one or more signals and (ii) a carbon dioxide stores model of the subject, a first capnometric component indicating a rate of metabolic carbon dioxide production corresponding to the full amount of carbon dioxide that leaves the subject for each breath, wherein the rate of metabolic carbon dioxide production is proportional to a whole-body metabolic activity;
    determining, with the one or more hardware processors, based at least in part on (i) the received one or more signals and (ii) the carbon dioxide stores model of the subject, a second capnometric component that is separate from the first capnometric component, the second capnometric component indicating a rate of carbon dioxide transfer to or from the tissue stores that correspond to a plurality of body compartments of the subject that store carbon dioxide, wherein the carbon dioxide stores model implements a model of the plurality of body compartments of the subject;
    tuning, with the one or more hardware processors, the model, during a test period, to match the measured carbon dioxide excretion rather than end-tidal carbon dioxide, to minimize a difference between a modeled carbon dioxide excretion and the measured carbon dioxide excretion during the test period;
    presenting, with the display, to a user the first capnometric component, the second capnometric component, and the measured carbon dioxide excretion;
    determining, with the one or more hardware processors, settings of a ventilator connected to the subject based on the first capnometric component; and
    using the determined settings to select, with the one or more hardware processors, a respiratory rate provided by the ventilator to the subject,
    wherein the modeled plurality of body compartments includes a heart, lungs, brain, blood, a muscle, fat, and kidneys of the subject.

2. The method of claim 1, wherein determining at least one of the first capnometric component and the second capnometric component further includes implementing, with the one or more hardware processors, the model of the plurality of body compartments of the subject, the model determining at least one of carbon dioxide production, carbon dioxide distribution, concentration of expired carbon dioxide, and end-tidal carbon dioxide.

3. The method of claim 2, wherein the model utilizes previously received information related to the rate of total carbon dioxide excreted by the subject to tune one or more model parameters relating to the modeled plurality of body compartments.

4. The method of claim 1, wherein the received one or more signals convey information related to the rate of total carbon dioxide excreted by the subject in real time or near real time.

5. A system for providing values of components of total carbon dioxide excreted by a subject, the system comprising:
    one or more hardware processors configured by machine readable instructions to:
    receive one or more signals from at least one carbon dioxide sensor conveying information related to a rate of the total carbon dioxide excreted by the subject, and determine a measured carbon dioxide excretion that corresponds to a full amount of carbon dioxide that leaves the subject for every breath, the measured carbon dioxide being a sum of metabolic carbon dioxide production and carbon dioxide released from tissue stores of the subject,
    implement a carbon dioxide stores model of the subject and tune the model, during a test period, to match a predicted model output with the measured carbon dioxide excretion, rather than end-tidal carbon dioxide, to minimize a difference between a modeled carbon dioxide excretion and the measured carbon dioxide excretion during the test period,
    determine, based at least in part on (i) the received one or more signals and (ii) the carbon dioxide stores model of the subject, a first capnometric component indicating a rate of metabolic carbon dioxide production corresponding to the full amount of carbon dioxide that leaves the subject for each breath, and a second capnometric component that is separate from the first capnometric component, the second capnometric component indicating a rate of carbon dioxide transfer to or from tissue stores that correspond to a plurality of body compartments of the subject that store carbon dioxide, wherein the rate of metabolic carbon dioxide production is proportional to a whole-body metabolic activity, wherein the carbon dioxide stores model implements a model of the plurality of body compartments of the subject, and
    provide, for presentation to a user, at least one of the first capnometric component and the second capnometric component; and
    a display configured to display the first capnometric component, the second capnometric component, and the measured carbon dioxide excretion,
    wherein the modeled plurality of body compartments includes a heart, lungs, brain, blood, a muscle, fat, and kidneys of the subject, and
    wherein the one or more hardware processors are configured by machine readable instructions to determine settings of a ventilator connected to the subject based on the first capnometric component and to use the determined settings to select a respiratory rate provided by the ventilator to the subject.

6. The system of claim 5, wherein the one or more hardware processors are further configured to model the plurality of body compartments of the subject to determine at least one of carbon dioxide production, carbon dioxide distribution, concentration of expired carbon dioxide, and end-tidal carbon dioxide.

7. The system of claim 6, wherein the one or more hardware processors are further configured to utilize previously received information related to the rate of total carbon dioxide excreted by the subject to tune one or more model parameters relating to the modeled plurality of body compartments.

8. The system of claim 6, wherein the one or more hardware processors are further configured to utilize the modeled plurality of body compartments for determining at least one of the first capnometric component and the second capnometric component.

9. The system of claim 5, wherein the received one or more signals convey information related to the rate of total carbon dioxide excreted by the subject in real time or near real time.

10. A system for providing values of components of total carbon dioxide excreted by a subject, the system comprising:
    one or more hardware processors configured to:
    cause data acquisition by at least one sensor for receiving one or more signals conveying information related to a rate of total carbon dioxide excreted by the subject and determine a measured carbon dioxide excretion that corresponds to a full amount of carbon dioxide that leaves the subject for every breath being a sum of metabolic carbon dioxide production and carbon dioxide released from tissue stores of the subject,
    cause implementation of a carbon dioxide stores model of the subject and tune the model, during a test period, to match a predicted model output with the measured carbon dioxide excretion, rather than end-tidal carbon dioxide, to minimize a difference between a modeled carbon dioxide excretion and the measured carbon dioxide excretion during the test period,
    determine, based at least in part on (i) the received one or more signals and (ii) the carbon dioxide stores model of the subject, a first capnometric component indicating a rate of metabolic carbon dioxide production corresponding to the full amount of carbon dioxide that leaves the subject for each breath, and a second capnometric component that is separate from the first capnometric component, the second capnometric component indicating a rate of carbon dioxide transfer to or from tissue stores that correspond to a plurality of body compartments of the subject that store carbon dioxide, wherein the rate of metabolic carbon dioxide production is proportional to a whole-body metabolic activity, and wherein the carbon dioxide stores model implements a model of the plurality of body compartments of the subject,
    determine settings of a ventilator connected to the subject based on the first capnometric component,
    use the determined settings to select a respiratory rate provided by the ventilator to the subject, and
    cause a display to present at least one of the first capnometric component and the second capnometric component to a user; and
    a display configured to display the first capnometric component, the second capnometric component, and the measured carbon dioxide excretion,
    wherein the modeled plurality of body compartments includes a heart, lungs, brain, blood, a muscle, fat, and kidneys of the subject.

11. The system of claim 10, wherein the one or more hardware processors determine the at least one of the first capnometric component and the second capnometric component by implementing the model of the plurality of body compartments of the subject,
    the one or more hardware processors determining, using the model, at least one of a carbon dioxide production and a carbon dioxide distribution.

12. The system of claim 11, wherein the model utilizes previously received information related to the rate of total carbon dioxide excreted by the subject to tune at least one model parameters relating to the modeled plurality of body compartments.

13. The system of claim 10, wherein the received one or more signals convey information related to the rate of total carbon dioxide excreted by the subject in real time or near real time.

* * * * *